US011559519B2

(12) United States Patent
Miwa et al.

(10) Patent No.: US 11,559,519 B2
(45) Date of Patent: *Jan. 24, 2023

(54) TIZANIDINE THERAPY SYSTEM

(71) Applicant: MEDRx Co., Ltd., Kagawa (JP)

(72) Inventors: Yasushi Miwa, Higashikagawa (JP); Hidetoshi Hamamoto, Higashikagawa (JP); Naoya Akazawa, Higashikagawa (JP); Takahiro Tanimoto, Higashikagawa (JP)

(73) Assignee: MEDRX, CO., LTD., Kagawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/965,758

(22) PCT Filed: Jan. 31, 2019

(86) PCT No.: PCT/JP2019/003453
§ 371 (c)(1),
(2) Date: Jul. 29, 2020

(87) PCT Pub. No.: WO2019/151423
PCT Pub. Date: Aug. 8, 2019

(65) Prior Publication Data
US 2021/0030724 A1 Feb. 4, 2021

(30) Foreign Application Priority Data

Jan. 31, 2018 (JP) .............. JP2018-016010
Jan. 31, 2018 (JP) .............. JP2018-016011
Feb. 1, 2018 (JP) .............. JP2018-016804
Feb. 1, 2018 (JP) .............. JP2018-016805

(51) Int. Cl.
*A61K 31/433* (2006.01)
*A61K 9/70* (2006.01)
*A61K 47/12* (2006.01)

(52) U.S. Cl.
CPC .......... *A61K 31/433* (2013.01); *A61K 9/7038* (2013.01); *A61K 47/12* (2013.01)

(58) Field of Classification Search
CPC ..... A61K 31/433; A61K 9/7038; A61K 47/12
See application file for complete search history.

(56) References Cited

U.S. PATENT DOCUMENTS

| 6,455,557 B1 | 9/2002 | Pellegrini et al. |
| 2004/0028724 A1 | 2/2004 | Terahara et al. |
| 2012/0114741 A1* | 5/2012 | Aung-Din ............ A61K 31/433 514/288 |
| 2017/0056502 A1 | 3/2017 | Miwa et al. |
| 2017/0056503 A1 | 3/2017 | Hamamoto et al. |
| 2018/0236082 A1 | 8/2018 | Miwa et al. |

FOREIGN PATENT DOCUMENTS

| EP | 1340496 A1 | 9/2003 |
| WO | 2004/112723 A2 | 12/2004 |
| WO | 1807033 * | 7/2016 |
| WO | 2017/038767 A1 | 3/2017 |

OTHER PUBLICATIONS

Henney III et al., "A clinically relevant review of tizanidine hydrochloride dose relationships to pharmacokinetics, drug safety and effectiveness in healthy subjects and patients," International Journal of Clinical Practice, 62 (2): 314-324 (2008).
Chantraine et al., "Modified Release Tizanidine in the Treatment of Spasticity," The Journal of International Medical Research, 16: 459-465 (1988).
Phase I Clinical Trial Results for MRX-4TZT in the United States, News Release dated Feb. 3, 2017.
International Search Report issued in corresponding International Patent Application No. PCT/JP2019/003453 dated Mar. 26, 2019.
International Preliminary Report on Patentability and Written Opinion issued in corresponding International Patent Application No. PCT/JP2019/003453 dated Aug. 4, 2020.
Extended European Search Report issued in corresponding European Patent Application No. 19746696.4 dated May 2, 2022.

* cited by examiner

*Primary Examiner* — Shirley V Gembeh
(74) *Attorney, Agent, or Firm* — Morgan, Lewis & Bockius LLP

(57) ABSTRACT

An object of the present invention is to provide a method for the treatment of a patient suffering from spasticity comprising administering to said patient a modified release dosage form comprising tizanidine or a pharmaceutically acceptable salt thereof.
The present invention relates to a method of administering a transdermal patch preparation comprising tizanidine or a pharmaceutically acceptable salt thereof to a subject in need thereof, wherein the transdermal patch preparation releases about 4 mg to about 36 mg of tizanidine or a pharmaceutically acceptable salt thereof for at least about 24 hours.

15 Claims, 7 Drawing Sheets

[FIG. 1]
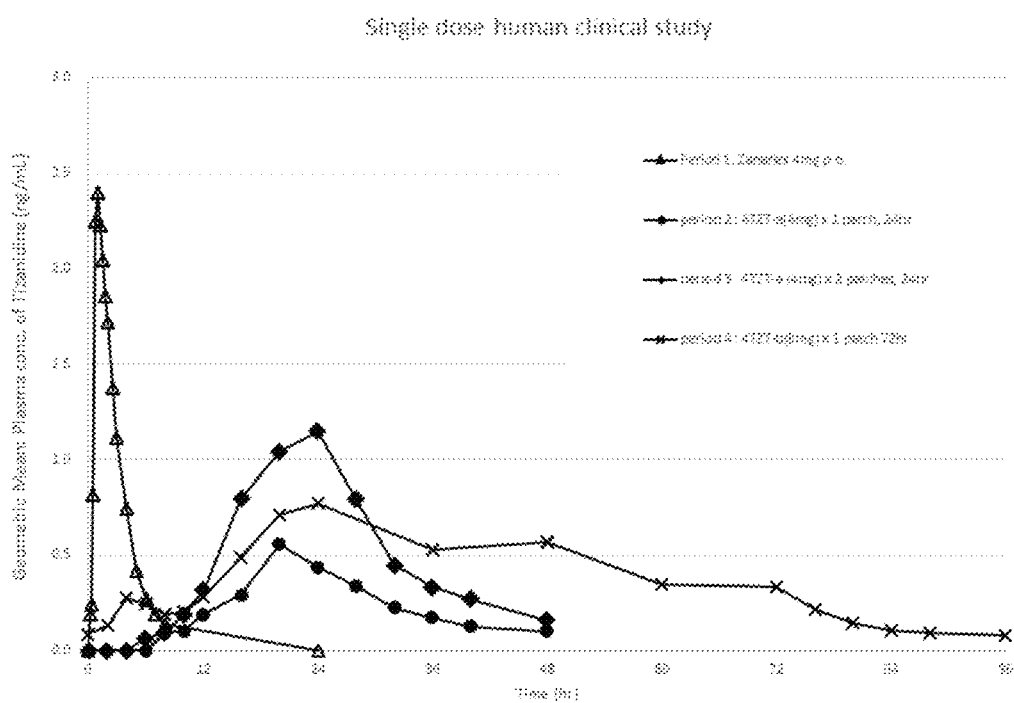

[FIG. 2]
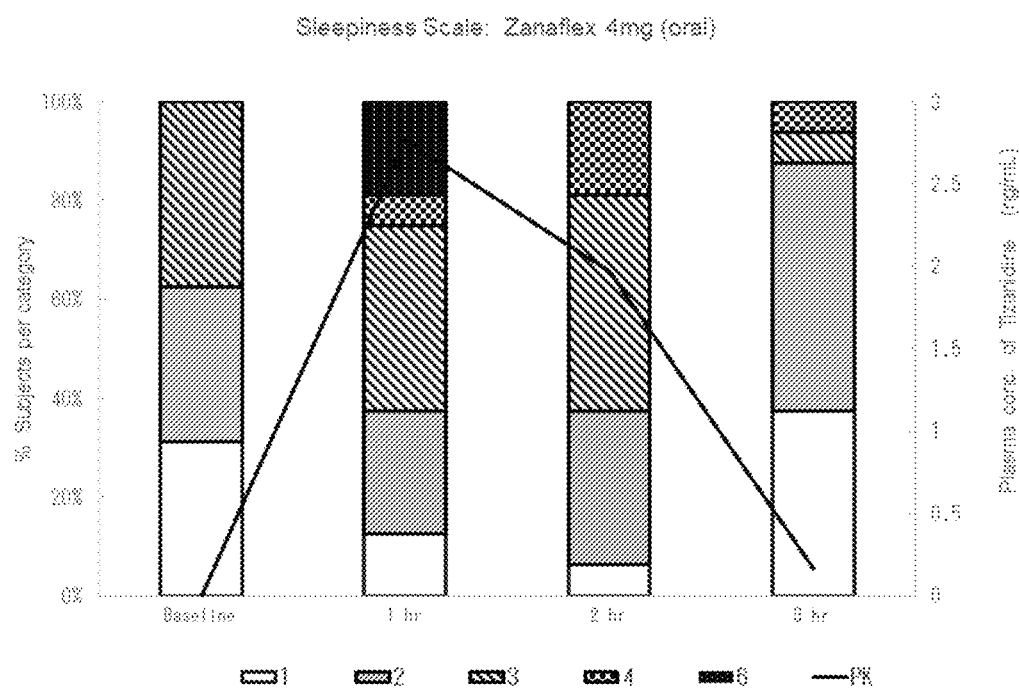

[FIG. 3]
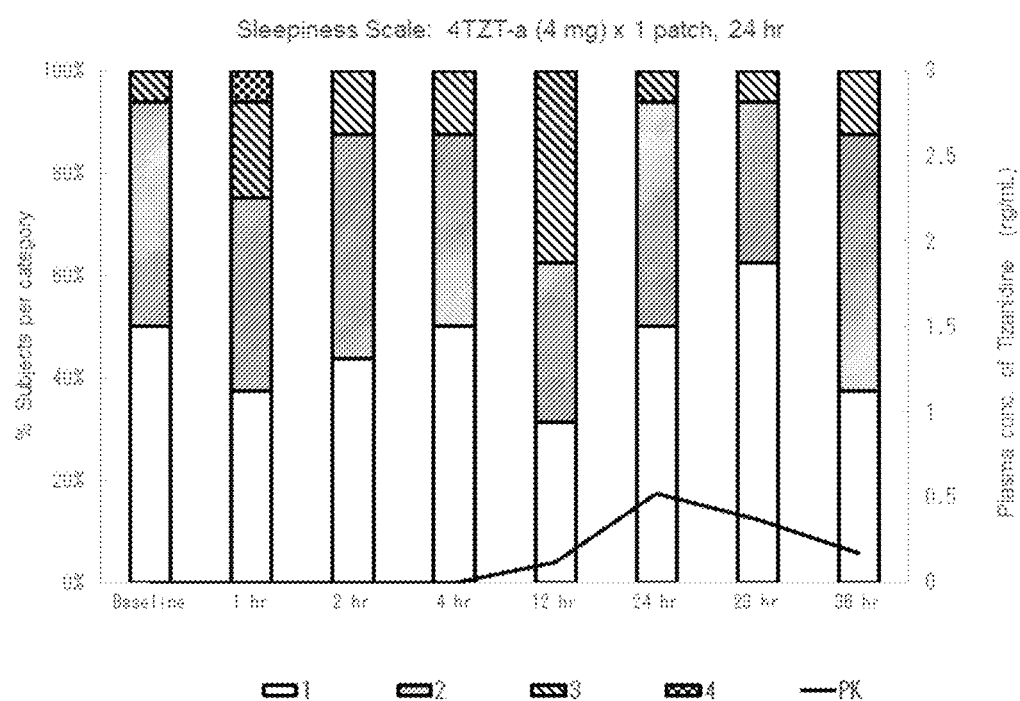

[FIG. 4]
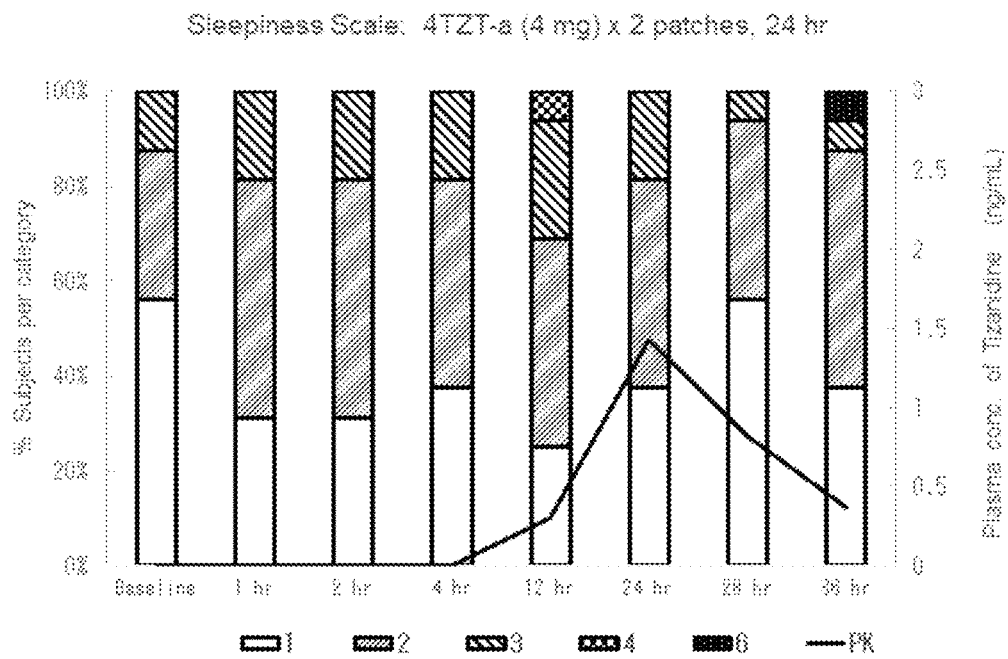
[FIG. 5]
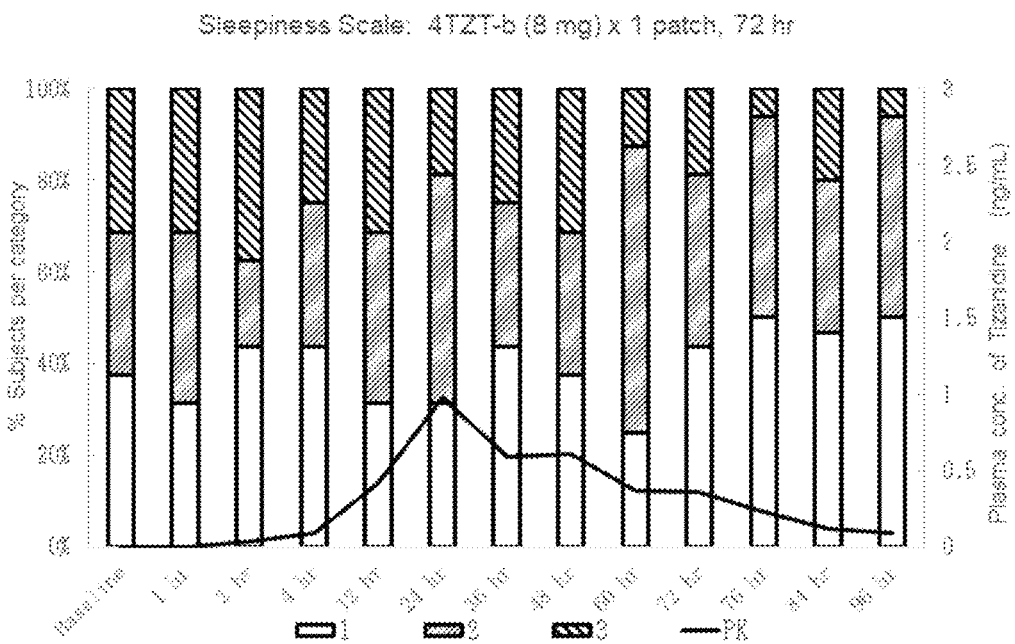

[FIG. 6]
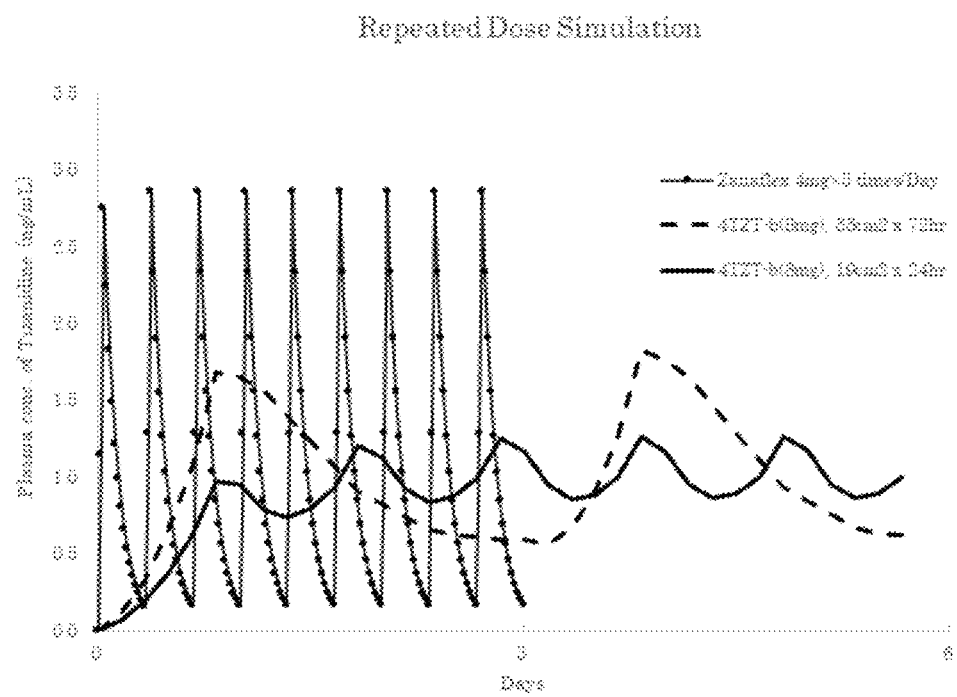
[FIG. 7]
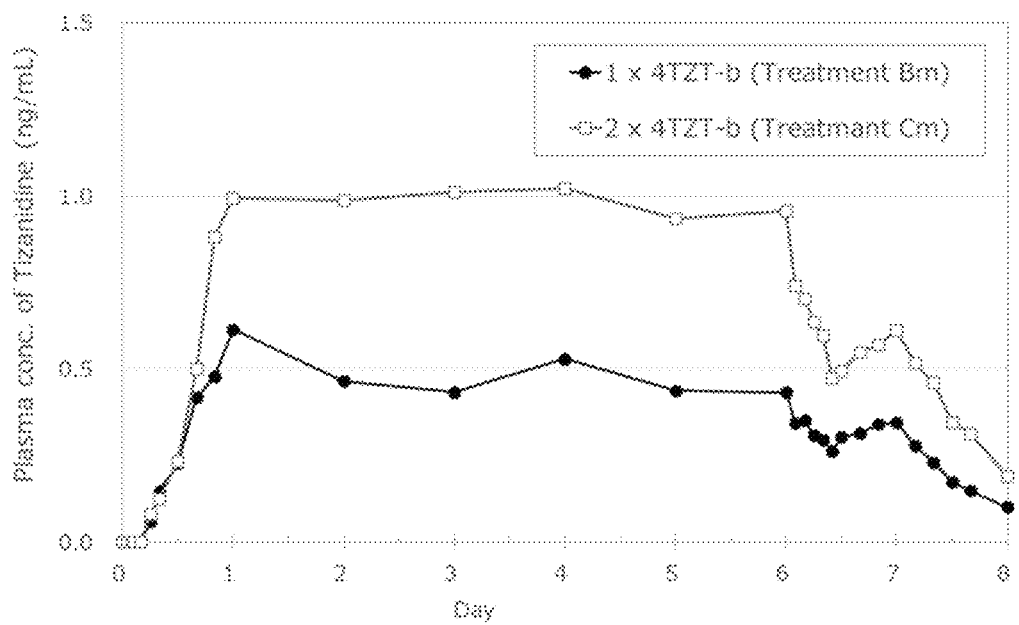

[FIG. 8]
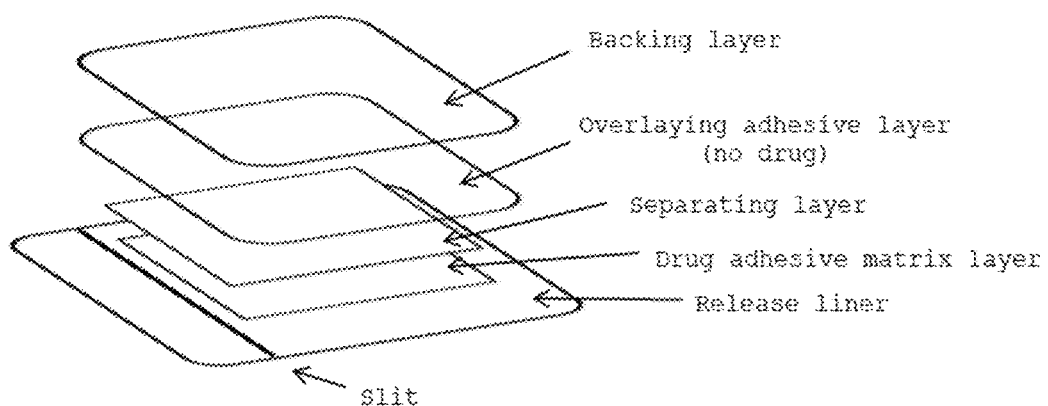
[FIG. 9]
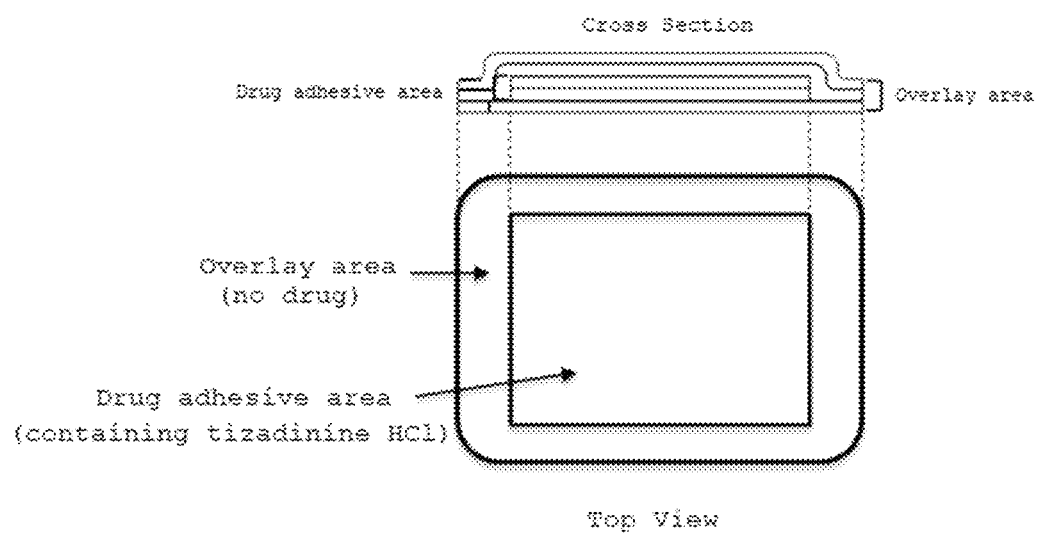

[FIG. 10]
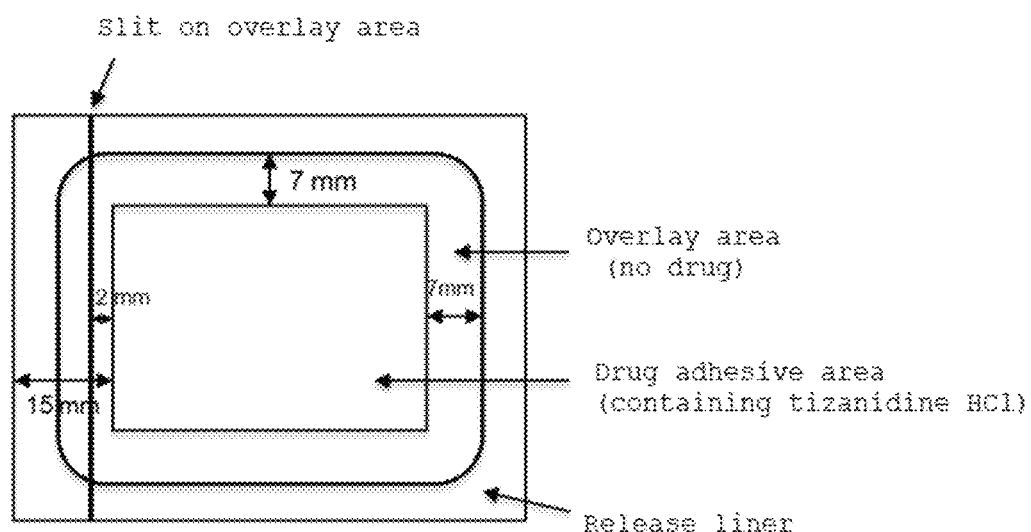

TIZANIDINE THERAPY SYSTEM

TECHNICAL FIELD

The present invention relates to a method of administering tizanidine to a subject in need thereof and a modified release dosage form comprising tizanidine or a pharmaceutically acceptable salt thereof. Specifically, the present invention relates to a method of administering tizanidine in the transdermal dosage form to a subject in need thereof.

BACKGROUND ART

Tizanidine is a central-acting $\alpha_2$ adrenoceptor agonist useful for treatment of spasticity in patients with upper motor neuron lesions resulting from cerebral or spinal injury, or certain other neurological conditions. Presently, an immediate release formulation of tizanidine (Zanaflex®) is dosed orally up to three times a day due to its short half-life. This frequent oral dosing leads to large fluctuations in the release profile of tizanidine, and subsequently, large fluctuations in the blood serum concentration of tizanidine. Side effects of immediate release tizanidine, such as somnolence, may be related to either the fluctuations in tizanidine concentration or excessively high tizanidine concentration, or both. According to Zanaflex® prescribing information, in multiple dose, placebo-controlled clinical studies, 48% of patients receiving any dose of tizanidine reported sedation as an adverse event versus 10% of patients receiving placebo. In 10% of this case, the sedation was rated as severe compared to <1% in the placebo treated patients. The patients are warned about performing activities requiring alertness, such as driving a vehicle or operating machinery while taking tizanidine (Zanaflex® prescribing information).

The sedating effects may interfere with everyday activity, and the effect appears to be dose related. According to Zanaflex® prescribing information, in a single dose study, 92% of the patients receiving 16 mg Zanaflex® orally, when asked, reported that they were drowsy during the 6-hour study as compared to 76% of the patients on 8 mg Zanaflex® and 35% of the patients on placebo. Patients noticed the onset of this effect 20 minutes following dosing. Of the patients who received a single dose of 16 mg, 51% continued to report drowsiness 6 hours following dosing compared to 13% in the patients receiving placebo or 8 mg of tizanidine.

Thus, there remains an unmet clinical need for a method of administering tizanidine to a patient that provides optimal dosing for effective management of spasticity and pain, with an improved side effect profile.

PRIOR ART DOCUMENTS

Patent Documents

Patent Document 1: U.S. Pat. No. 6,455,557 B

Non-Patent Documents

Non-Patent Document 1: A Clinically relevant review of tizanidine hydrochloride dose relationships to pharmacokinetics, drug safety and effectiveness in healthy subjects and patients (Int J Clin Pract, February 2008, 62, 2, 314-324)

Non-Patent Document 2: Modified Release Tizanidine in the Treatment of Spasticity (The Journal of International Medical Research 1998; 16: 459-465)

SUMMARY OF THE INVENTION

Problems to be Solved

An object of the present invention is to provide a method for the treatment of a patient suffering from a musculoskeletal disease or disorder (e.g., spasticity, fibromyalgia, myofascial pain, tension headaches, neuropathic pain, etc.), which comprises administering to said patient a modified release dosage form comprising tizanidine or a pharmaceutically acceptable salt thereof.

Another object of the present invention is to provide a method of administering a transdermal patch preparation comprising tizanidine or a pharmaceutically acceptable salt thereof to a patient to reduce undesirous side effects.

Yet another object of the present invention is to provide a method of administering a transdermal patch preparation comprising tizanidine or a pharmaceutically acceptable salt thereof which provides a continuous dosing of the drug to the patient for at least about 24 hours.

Yet another object of the present invention is to provide a method of administering a transdermal patch preparation comprising tizanidine or a pharmaceutically acceptable salt thereof wherein the bioavailability of tizanidine or a pharmaceutically acceptable salt thereof is increased by transdermal administration relative to administration of a comparable dosage of tizanidine or a pharmaceutically acceptable salt thereof in an oral dosage form.

Accordingly, it can be understood that the transdermal patch preparation comprising tizanidine or a pharmaceutically acceptable salt thereof of the present invention is useful to reduce the side effects accompanied with the oral administration of tizanidine or a pharmaceutically acceptable salt thereof. Moreover, the transdermal patch preparation comprising tizanidine or a pharmaceutically acceptable salt thereof of the present invention has excellent skin permeation rate of the drug and shows high bioavailability compared to its oral administration and greatly diminish absorption variability between patients, thus being expected that it can be substituted for the conventional administration route of tizanidine.

Means for Solving the Problems

It has surprisingly been found that the side effects such as somnolence and dizziness observed with oral administration of tizanidine are remarkably reduced by controlling pharmacokinetic parameters of tizanidine via transdermal administration of the drug.

Effects of the Invention

According to the present invention, the side effects such as somnolence and dizziness observed with the oral administration of tizanidine can be reduced.

BRIEF DESCRIPTION OF THE DRAWINGS

FIG. 1 is a graph that illustrates the plasma concentration of tizanidine obtained by a single dose human clinical study.

FIG. 2 illustrates the expression rate of sleepiness at a single-dose oral administration clinical study.

FIG. 3 illustrates the expression rate of sleepiness at a single-dose transdermal administration clinical study.

FIG. 4 illustrates the expression rate of sleepiness at a single-dose transdermal administration clinical study.

FIG. 5 illustrates the expression rate of sleepiness at a single-dose transdermal administration clinical study.

FIG. 6 illustrates the simulated plasma concentration of tizanidine in the multiple dose therapy.

FIG. 7 illustrates the plasma concentration of tizanidine obtained by a multiple dose human clinical study.

FIG. 8 illustrates a composition of tizanidine transdermal system.

FIG. 9 illustrates a diagram of tizanidine transdermal system.

FIG. 10 illustrates a diagram (overlay and release liner design) of tizanidine transdermal system.

DESCRIPTION OF EMBODIMENTS

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used herein, the singular forms "a", "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about", it will be understood that the particular value forms another embodiment. It will be further understood that the endpoints of each of the ranges are significant both in relation to the other endpoint, and independently of the other endpoint.

The term "optional" or "optionally" means that the subsequently described event or circumstance may or may not occur, and that the description includes instances where said event or circumstance occurs and instances where it does not.

As used herein, the term "comprise" and variations of the term, such as "comprising" and "comprises" means "including but not limited to" and is not intended to exclude, for example, other additives, components, integers or steps. The term "exemplary" means "an example of" and is not intended to convey an indication of a preferred or ideal embodiment. The term "such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As used herein, the term "tizanidine" is used in broad sense to include not only "tizanidine" per se as a free base but also its pharmaceutically acceptable physical forms thereof. Suitable pharmaceutically acceptable physical forms include pharmaceutically acceptable salts, pharmaceutically acceptable solvates, pharmaceutically acceptable hydrates, pharmaceutically acceptable anhydrates, pharmaceutically acceptable isomers, pharmaceutically acceptable polymorphs, pharmaceutically acceptable complexes and the like.

The pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, nitric acids and the like; salts formed with organic acids such as acetic, oxalic, tartaric, succinic, maleic, fumaric, gluconic, citric, malic, methanesulfonic, p-toluenesulfonic, napthalenesulfonic, polygalacturonic acids and the like; salts formed from elemental anions such as chloride, bromide and iodide; salts formed from metal hydroxides such as sodium hydroxide, potassium hydroxide, calcium hydroxide, lithium hydroxide and magnesium hydroxide; salts formed from metal carbonates such as sodium carbonate, potassium carbonate, calcium carbonate and magnesium carbonate; salts formed from metal bicarbonates such as sodium bicarbonate and potassium bicarbonate; salts formed from metal sulfates such as sodium sulfate and potassium sulfate; and salts formed from metal nitrates such as sodium nitrate and potassium nitrate. Preferably, the pharmaceutically acceptable salt is hydrochloride.

As used herein, the term "sorbate component" means sorbic acid in the free form and/or a metal salt of sorbic acid. Examples of the metal salt of sorbic acid include sodium sorbate, potassium sorbate and calcium sorbate. The metal salt of sorbic acid is preferably potassium sorbate.

In case where sorbic acid or a metal salt of sorbic acid is used alone, the sorbate component denotes sorbic acid or the metal salt of sorbic acid. In case where sorbic acid and a metal salt of sorbic acid are used in combination, the sorbate component denotes sorbic acid and the metal salt of sorbic acid.

In case where sorbic acid or a metal salt of sorbic acid is used alone, the term "concentration of sorbate component" as used herein denotes the concentration of sorbic acid or the metal salt. In case where sorbic acid and a metal salt of sorbic acid are used in combination, the concentration denotes the concentration of sorbic acid and the metal salt of sorbic acid.

The term "modified release dosage form" as used herein includes any one of oral dosage form, nasal dosage form, transmucosal dosage form and transdermal dosage form as long as the particular pharmacokinetic parameters of tizanidine as defined below are obtained.

The term "transdermal" (or "percutaneous") as used herein means that a drug is delivered by the passage into the skin or mucosal tissue and through the skin or mucosal into the systemic circulation. Hence, the terms "transdermal" and "transmucosal" are used interchangeably unless otherwise specified.

The term "therapeutically effective amount" of tizanidine as used herein means a nontoxic and sufficient amount of tizanidine to provide a desired therapeutic effect. The desired therapeutic effect is the alleviation of pain and spasticity.

The term "elimination rate constant" as used herein means apparent first-order terminal elimination rate constant calculated from a semi-log plot of the plasma concentration versus time curve, calculated by linear least-squares regression analysis using the maximum number of points in the terminal log linear phase.

In one embodiment, the invention discloses a method for the treatment of a patient suffering from spasticity comprising administering to said patient a modified release dosage form comprising tizanidine or a pharmaceutically acceptable salt thereof.

In one embodiment, the invention discloses a method for the treatment of a patient suffering from spasticity comprising administering to said patient a transdermal dosage form comprising tizanidine or a pharmaceutically acceptable salt thereof.

The transdermal dosage form may be an aqueous or non-aqueous patch preparation. The patch preparation may be a patch comprising a support and an adhesive layer on one surface of the support. The adhesive layer (also referred to as "drug adhesive matrix" or "drug matrix area") may comprise tizanidine hydrochloride, an organic solvent, a percutaneous absorption accelerator, a basic component and a plaster.

In some embodiments, the patch preparation may include 1) a backing layer, 2) an overlaying adhesive layer containing no drug, 3) a separating layer, 4) a drug adhesive matrix and 5) a release liner. In further specific embodiments, the backing layer may be a non-woven backing. In further specific embodiments, the separating layer may be a non-woven backing. In further specific embodiments, the release liner may have a slit on the overlay area, that is, a design that enables the patch preparation to be applied to the skin without touching the drug adhesive matrix. In further specific embodiments, the drug adhesive matrix may contain about 0.4 mg/cm$^2$ to about 0.8 mg/cm$^2$ of tizanidine hydrochloride as the drug (equivalent to about 0.34 mg/cm$^2$ to about 0.69 mg/cm$^2$ tizanidine base). In further specific embodiments, the patch preparation may be packaged in a polyethylene aluminum-laminated pouch.

In some embodiments, the amount of tizanidine or a pharmaceutically acceptable salt thereof in the composition may range from about 0.5% to about 10% by weight or about 1% to about 5% by weight of the total amount of the dried adhesive layer. The dosage amount of tizanidine or a pharmaceutically acceptable salt thereof in the composition may range from about 2 mg to about 128 mg, about 6 mg to about 72 mg, about 8 mg to about 56 mg or about 4 mg to about 50 mg.

In some embodiments, the organic solvent may be an aliphatic acid, an alcohol, an ester compound, and an amide compound or a combination thereof.

Examples of the aliphatic acid include levulinic acid, sorbic acid, capric acid, lauric acid, myristic acid, palmitic acid, stearic acid, isostearic acid, and oleic acid.

Examples of the alcohol include a monovalent alcohol such as lauryl alcohol, myristyl alcohol, oleyl alcohol, isostearyl alcohol and cetyl alcohol; a divalent alcohol such as propylene glycol, butylene glycol, dipropylene glycol, diisobutylene glycol, polyethylene glycol and hexylene glycol; and a trivalent alcohol such as glycerin and hexanetriol. In some embodiments, the alcohol is oleyl alcohol.

Examples of the ester compound include diethyl sebacate, methyl laurate, diisopropyl adipate, isopropyl myristate and medium-chain fatty acid triglyceride.

In some embodiments, the percutaneous absorption accelerator may be sorbate component. The sorbate component may be sorbic acid and/or a metal salt of sorbic acid. Examples of the metal salt of sorbic acid include an alkali metal salt such as potassium sorbate and sodium sorbate; an alkali earth metal salt such as calcium sorbate. In some embodiments, the percutaneous absorption accelerator may be potassium sorbate.

The concentration of the sorbate component can be about 0.5 to about 3.5 mol, about 0.6 to about 3.5 mol, about 0.7 to about 3.5 mol, about 0.8 to 3.5 mol, about 0.9 to about 3.5 mol, about 1.0 to about 3.5 mol, about 1.1 to about 3.4 mol, about 1.1 to about 3.3 mol, about 1.1 to about 3.2 mol, about 1.1 to about 3.1 mol, about 1.1 to about 3.0 mol, about 1.2 to about 3.0 mol, about 1.3 to about 3.0 mol, about 1.4 to about 3.0 mol, about 1.5 to about 3.0 mol, about 1.6 to about 3.0 mol, about 1.7 to about 3.0 mol, about 1.8 to about 3.0 mol, about 1.8 to about 3.0 mol, about 1.9 to about 3.0 mol, about 2.0 to about 3.0 mol, about 2.2 to about 2.8 mol, about 2.3 to about 2.7 mol, about 2.0 to about 2.5 mol or about 2.5 to about 3.0 mol per mol of tizanidine or a pharmaceutically acceptable salt thereof.

In case where the sorbate component is a combination of sorbic acid and a metal salt of sorbic acid, the concentration of the sorbic acid can be about 0.1 to about 2.5 mol, about 0.2 to about 2.0 mol, about 0.3 to about 1.6 mol, about 0.4 to about 1.5 mol or about 0.6 to about 1.2 mol per mol of tizanidine or a pharmaceutically acceptable salt thereof, and the concentration of the metal salt of sorbic acid can be about 0.5 to about 2.5 mol, about 0.6 to about 2.4 mol, about 0.6 to about 2.0 mol, about 0.6 to about 1.8 mol, about 0.8 to about 1.7 mol, about 0.9 to about 1.8 mol or about 0.9 to about 1.6 mol per mol of tizanidine or a pharmaceutically acceptable salt thereof.

In some embodiments, the basic component may include one or more of organic basic compounds, inorganic basic compounds, and salts of strong base.

Examples of the organic basic compound include a $C_{2-9}$ alkanolamine such as monoethanolamine, monoisopropanolamine, diethanolamine, diisopropanolamine, triethanolamine, triisopropanolamine, ethylenediamine and trishydroxymethylaminomethane (trometamol); and a basic amino acid such as arginine.

Examples of the inorganic basic compound include a hydroxide such as sodium hydroxide, potassium hydroxide and calcium hydroxide.

Examples of the salt of strong base include a metal salt of carboxylic acid such as sodium benzoate, sodium propionate, calcium propionate, sodium fumarate, sodium sorbate and potassium sorbate; a metal salt of hydroxyl acid such as sodium lactate, sodium tartrate, potassium tartrate and sodium citrate; sodium sulfite; and sodium pyrosulfite.

In some embodiments, the plaster may comprise a polymer. Examples of the polymer include an acrylic polymer, a rubber polymer, a silicone polymer and a vinyl ether-based polymer. In some embodiments, a rubber polymer such as styrene-isoprene-styrene block copolymer, styrene-butadiene-styrene block copolymer, polyisoprene, polyisobutylene and/or polybutadiene can be utilized. The concentration of the rubber polymer may be about 5% to about 40% by weight or about 5% to about 25% by weight of the total weight of the dried adhesive layer.

In some embodiments, the drug adhesive matrix may further comprise a filler. The concentration of the filler can be about 0.5% to about 5% by weight of the total weight of the adhesive layer. In some embodiments, the filler may be fumed silica. AEROSIL® is an example of commercially available fumed silica.

The drug adhesive matrix may further contain other additive such as a tackifier resin, a softener and an antioxidant. In some embodiments, the tackifier resin may be terpene resin. In some embodiments, the softener may be liquid paraffin. Examples of the antioxidant include dibutylhydroxytoluene, ascorbic acid, propyl gallate, sodium sulfite and sodium pyrosulfite.

The drug adhesive matrix can be of any suitable and appropriate thickness. In some embodiments, the thickness of the drug adhesive matrix may be about 20 to about 600 μm, about 50 to about 500 μm, about 100 to about 400 μm, about 150 to about 350 μm or about 200 to about 300 μm.

In some embodiments, the surface area of the transdermal patch preparation is sufficient to maintain the effective contact with the skin during administration, and also provides an intended drug delivery rate. The surface area of the drug adhesive matrix to be contacted with the skin may be changed, and the surface area itself can be of any suitable and appropriate size. The surface area of the drug adhesive matrix may be, for example, about 10 to about 200 square centimeters, and preferably about 20 to about 120 square centimeters. In one embodiment, the surface area of the drug adhesive matrix may be about 20 square centimeters, about 40 square centimeters, about 80 square centimeters or about 120 square centimeters.

The surface area of the patch preparation may increase upon the inclusion of an adhesive overlay (also referred to as "overlay area") on the top of the drug adhesive matrix. The patch preparation of the present invention, which is generally pale yellow to yellow in color, may be square, circular, rectangular or triangular in shape or may be of other shapes. The adhesive overlay comprises an adhesive layer which doesn't contain any active ingredient and exhibits an excellent adhesive strength.

The thickness of the adhesive overlay can be of any suitable and appropriate dimension. For example, the thickness of the adhesive overlay may be about 50 to about 500 μm, about 75 to about 400 μm or about 120 to about 300 μm.

The surface area of the transdermal patch preparation comprising the overlay area can be of any suitable and appropriate size. In some embodiments, the surface area of the transdermal patch preparation comprising the overlay area may be about 10 to about 200 square centimeters, preferably from about 20 to about 155 square centimeters. In one embodiment, the surface area of the transdermal patch preparation comprising the overlay area may be about 36 square centimeters, about 62 square centimeters, about 110 square centimeters or about 155 square centimeters.

In preferred embodiments, the transdermal patch preparation of the present invention is the following:

Patch preparation 1, in which the surface of the matrix to be applied to the skin has an area of about 20 square centimeters, comprises about 9.2 mg of tizanidine hydrochloride (equivalent to about 8 mg tizanidine base) in the matrix adhesive composition.

In specific embodiments, the aforesaid patch preparation 1 is applied once daily to a patient in need thereof and is suitable for achieving a tizanidine release of up to about 6 mg/24 hours. In further specific embodiments, the aforesaid patch preparation 1 is applied once daily to a patient in need thereof and is suitable for achieving a tizanidine release of about 2 mg/24 hours to about 6 mg/24 hours. In further specific embodiments, the aforesaid patch preparation 1 is applied once daily to a patient in need thereof and is suitable for achieving a tizanidine release of about 6 mg/24 hours.

Patch preparation 2, in which the surface of the matrix to be applied to the skin has an area of about 40 square centimeters, comprises about 18.4 mg of tizanidine hydrochloride (equivalent to about 16 mg tizanidine base) in the matrix adhesive composition.

In specific embodiments, the aforesaid patch preparation 2 is applied once daily to a patient in need thereof and is suitable for achieving a tizanidine release of up to about 12 mg/24 hours. In further specific embodiments, the aforesaid patch preparation 2 is applied once daily to a patient in need thereof and is suitable for achieving a tizanidine release of about 4 mg/24 hours to about 12 mg/24 hours. In further specific embodiments, the aforesaid patch preparation 2 is applied once daily to a patient in need thereof and is suitable for achieving a tizanidine release of about 12 mg/24 hours.

Patch preparation 3, in which the surface of the matrix to be applied to the skin has an area of about 80 square centimeters, comprises about 36.8 mg of tizanidine hydrochloride (equivalent to about 32 mg tizanidine base) in the matrix adhesive composition.

In specific embodiments, the aforesaid patch preparation 3 is applied once daily to a patient in need thereof and is suitable for achieving a tizanidine release of up to about 24 mg/24 hours. In further specific embodiments, the aforesaid patch preparation 3 is applied once daily to a patient in need thereof and is suitable for achieving a tizanidine release of about 8 mg/24 hours to about 24 mg/24 hours. In further specific embodiments, the aforesaid patch preparation 3 is applied once daily to a patient in need thereof and is suitable for achieving a tizanidine release of about 24 mg/24 hours.

Patch preparation 4, in which the surface of the matrix to be applied to the skin has an area of about 120 square centimeters, comprises about 55.2 mg of tizanidine hydrochloride (equivalent to about 48 mg tizanidine base) in the matrix adhesive composition.

In specific embodiments, the aforesaid patch preparation 4 is applied once daily to a patient in need thereof and is suitable for achieving a tizanidine release of up to about 36 mg/24 hours. In further specific embodiments, the aforesaid patch preparation 4 is applied once daily to a patient in need thereof and is suitable for achieving a tizanidine release of about 12 mg/24 hours to about 36 mg/24 hours. In further specific embodiments, the aforesaid patch preparation 4 is applied once daily to a patient in need thereof and is suitable for achieving a tizanidine release of about 36 mg/24 hours.

Various occlusive and non-occlusive, flexible and non-flexible backing members or overlays can be used in the patch preparation of the present invention, if desired. The backing of the transdermal patch preparation should be nonirritating to the human skin and can be manufactured from any suitable material(s), provided the transdermal patch preparation effectively retains the composition of the adhesive layer and does not change during the manufacturing, shipment, storage and use. When an appropriate backing is selected, the transdermal patch preparation does not change during use even if the backing is flexible, bendable, and pliable. While the backing of the transdermal patch preparation can be manufactured from any suitable material (s), the backing is typically a self-supporting sheet of water-soluble or water insoluble, woven or non-woven, polymeric or natural, durable material that provides strength and integrity for the composition of the adhesive layer.

In specific embodiments, the suitable material forms a flexible, bendable, pliable, and/or stretchable backing. The backing can include a porous or non-porous sheet of water soluble or water insoluble material that provides a support for the adhesive skin patch preparation. Alternatively, the backing can include water soluble or water insoluble polymeric fibers, a porous film, or any other kind of matrix with spaces within the matrix. Specific backing includes a lightweight, porous, pliable strip composed of a nonwoven fabric of polymeric or natural fibers such as polyester and cotton, or cellulose fibers optionally bonded together with a sizing resin. In specific embodiments, the backing includes non-woven fabric. In specific embodiments, the polymeric fibers can include polyethylene terephthalate (PET or PETE). For example, the backing can include cellophane, cellulose acetate, ethylcellulose, plasticized vinyl acetate-vinyl chloride copolymer, polyethylene terephthalate (PET), nylon, polyethylene, polypropylene, polyvinylidene chloride, ethylene vinyl acetate, paper, cloth, non-woven fabric, foam and aluminum foil.

To prevent the passage of drug away from the exposed surface of a patch preparation of the invention prior to its use, the surface of the patch preparation generally can be covered with a protective release film or foil, for example, waxed paper. The release film may be a polymer film or sheet treated with an appropriate release agent. The polymer film or sheet may be composed of cellulose acetate, ethylcellulose, plasticized vinyl acetate-vinylchloride copolymer, polyethylene terephthalate (PET), nylon, polyethylene, polypropylene, polyvinylidene chloride, and/or ethylene vinyl acetate.

The transdermal patch preparation is typically packaged in an unit dose pouch that puts 1 patch preparation inside a sealed and printed pouch. The pouching material of the present invention is a multi-laminate film whose outermost layer is printable layer and inner-most layer is heat sealable layer with a protective foil layer in between to provide barrier function, and may be free of an oxygen scavenger, a desiccant, or any other stabilizing material. The selected pouching material has characteristics of stability and acceptable heat sealability protected during transportation.

In one embodiment, the method of delivering tizanidine or a pharmaceutically acceptable salt to a patient comprises providing a transdermal patch preparation of the present invention; placing the transdermal patch preparation on the patient's skin; and continuously applying the patch preparation to the skin for a sufficient time to enable the systemic delivery of tizanidine or a pharmaceutically acceptable salt thereof and/or achieve the desired therapeutic effect.

The patch preparation of the present invention is applied to the patient's skin and should be in firm contact therewith so that the patch preparation adheres to the skin. The patch preparation may be applied to each site of a patient, for example, the back, upper/middle/lower arm, abdomen, thigh, behind an ear, chest or shoulder.

In some embodiments, the transdermal patch preparation may be repeatedly applied to a patient. The number of the application may be once a day, twice a day, once every two days, once every three days, once every four days, once every 6 days or once a week.

In some embodiments, the transdermal patch preparation may be applied to the skin once a day, and can adhere to the skin for about 24 hours. In another embodiment, the transdermal patch preparation may be applied once every three days, and can adhere to the skin for about 72 hours.

In one embodiment, the method of administering tizanidine or a pharmaceutically acceptable salt thereof as used herein may be defined by some pharmacokinetic parameters determined by a human pharmacokinetic study using a modified release dosage form.

In some embodiments, the elimination rate constant of tizanidine determined by a single dose or a multiple dose human pharmacokinetic study may be about 0.01 to about 0.2, about 0.02 to about 0.18, about 0.03 to about 0.15, about 0.05 to about 0.10. When a transdermal dosage form is used as a dosage form, the elimination rate constant should be defined at any point after removal or disappearance of the dosage form from human skin.

In some embodiments, $T_{max}$ of tizanidine determined by a single dose human pharmacokinetic study may be about 12 hours to 48 hours. In some embodiments, $T_{max}$ of tizanidine determined by a single-dose human pharmacokinetic study may be about 24 hours.

In some embodiments, the maximum plasma concentration ($C_{max}$) and $AUC_{0-inf}$ (the area under the plasma concentration curve from time 0 to infinity) provided by a single dose administration of a modified release dosage form comprising tizanidine or a pharmaceutically acceptable salt thereof satisfy the following condition. That is, the value represented by the following formula is at least 5 hours, at least 10 hours, or at least 15 hours.

$$(AUC_{0-inf})/(C_{max})$$

In some embodiments, when the dosage form is a transdermal dosage form, $AUC_{0-inf}$ (the area under the plasma concentration curve from time 0 to infinity) provided by a single dose administration of a modified release dosage form comprising tizanidine or a pharmaceutically acceptable salt thereof may be at least 1.0 ng*h/ml per mg of tizanidine, at least 1.5 ng*h/ml per mg of tizanidine, or at least 2.0 ng*h/ml per mg of tizanidine.

In multiple dose administration, the plasma concentration of tizanidine may reach steady state. In some embodiments, $C_{ss,max}$ (the maximum plasma concentration at steady state) and $C_{ss,min}$ (the minimum plasma concentration at steady state) satisfy the following formula:

$$\frac{(Css, \max - Css, \min)}{Css, \max} < 0.9.$$

In some embodiments, when the dosage form is applied once a day, the value calculated from the following formula (1) may be less than 0.9, less than 0.8, less than 0.7, less than 0.6, less than 0.5, less than 0.4, or less than 0.3.

$$\frac{(Css, \max - Css, \min)}{Css, \max} \qquad (1)$$

In some embodiments, the $C_{ss,max}$ may be about 0.01 to about 0.5 ng/mL per mg of tizanidine a day, preferably about 0.02 to about 0.4 ng/mL per mg of tizanidine a day, more preferably about 0.025 ng/mL to about 0.245 ng/mL per mg of tizanidine a day.

As used herein, the "$C_{ss,max}$ per mg of tizanidine" is calculated for each single dosage amount. In other word, when P mg per dose of tizanidine is administered, "$C_{ss,max}$ per mg of tizanidine" is obtained by dividing $C_{ss,max}$ by P. The similar calculating method is also applied on "$C_{ss,min}$ per mg of tizanidine".

In some embodiments, the $C_{ss,min}$ may be about 0.01 to about 0.3 ng/mL per mg of tizanidine a day, preferably about 0.01 to about 0.2 ng/mL per mg of tizanidine a day, more preferably about 0.01 to about 0.1 ng/mL per mg of tizanidine a day.

In some embodiments, when the dosage form is applied once a day, the $C_{ss,min}$ may be about 0.03 to about 0.30 ng/mL per mg of tizanidine a day, about 0.04 to about 0.25 ng/mL per mg of tizanidine a day, about 0.05 to about 0.20 ng/mL per mg of tizanidine a day, or about 0.07 to about 0.15 ng/mL per mg of tizanidine a day.

In some embodiments, the $C_{ss,min}$ may be less than about 0.3 ng/mL per mg of tizanidine a day, less than about 0.2 ng/mL per mg of tizanidine a day, or about 0.1 ng/mL per mg of tizanidine a day.

In one embodiment, the process of preparing the transdermal patch preparation comprises preparing a drug mass comprising tizanidine or a pharmaceutically acceptable salt thereof, an adhesive material and one or more pharmaceutically acceptable excipients; casting the drug mass onto a release liner film; drying the release liner and the drug mass to form an adhesive layer on the release liner; laminating a backing layer to the adhesive layer; slitting and trimming the laminated coating layer; and die-cutting the laminated product into dosage units with a fixed size rotary die cutter.

EXAMPLES

The present invention is further illustrated by the following examples which are provided to be exemplary of the invention and do not limit the scope of the invention.

I. Preparation of Dermal Patch Preparation

Transdermal patch preparations comprising tizanidine were prepared using the ingredients and relative amounts thereof shown in Table 1 below (Preparation Examples 1-4). Tizanidine hydrochloride, sorbic acid, potassium sorbate, oleic acid, oleyl alcohol, concentrated glycerin, purified water, propylene glycol, butylene glycol, sodium sulfite, propyl gallate and liquid paraffin were mixed and then dissolved to yield a homogeneous solution. Terpene resin, styrene-isoprene-styrene block copolymer and AEROSIL® (fumed silica) were added thereto and uniformly mixed to yield an adhesive composition containing the active ingredient. The resulting adhesive composition was coated onto the PET film. The composition was then dried to eliminate toluene and yield an adhesive layer containing the active ingredient.

TABLE 1

| Ingredient | Preparation Example 1 | Preparation Example 2 | Preparation Example 3 | Preparation Example 4 |
|---|---|---|---|---|
| Tizanidine Hydrochloride | 1.72 | 1.72 | 1.72 | 1.72 |
| Sorbic acid | 0 | 0.66 | 0.66 | 0.33 |
| Potassium sorbate | 0.89 | 0.89 | 1.34 | 0.89 |
| Oleic acid | 1.5 | 1.5 | 1.5 | 1.5 |
| Oleyl alcohol | 10.0 | 10.0 | 10.0 | 10.0 |
| Concentrated glycerin | 5.0 | 5.0 | 5.0 | 5.0 |
| Purified water | 0.5 | 0.5 | 0.5 | 0.5 |
| Propylene glycol | 8.0 | 8.0 | 8.0 | 8.0 |
| Butylene glycol | 3.0 | 3.0 | 3.0 | 3.0 |
| AEROSIL® | 3.0 | 3.0 | 3.0 | 3.0 |
| Liquid paraffin | 22.24 | 21.58 | 21.13 | 21.91 |
| Terpene resin | 28 | 28 | 28 | 28 |
| Stylene-isoprene-stylene block copolymer | 16 | 16 | 16 | 16 |
| Sodium sulfite | 0.1 | 0.1 | 0.1 | 0.1 |
| Propyl gallate | 0.05 | 0.05 | 0.05 | 0.05 |
| Total | 100.0 | 100.0 | 100.0 | 100.0 |

II. Single-Dose Pharmacokinetic Study & Steady-State Simulation

A comparative pharmacokinetics study of the transdermal patch preparation comprising tizanidine (4TZT) was conducted. Specifically, an open-label, fixed-sequence, 4-period, PK study was conducted. Subjects received each treatment in affixed sequence, specifically the single oral dose of 4 mg tizanidine capsule in Period 1 (Treatment A), the single application of 1 transdermal patch preparation comprising 4 mg tizanidine (hereinafter also defined as "4TZT-a") following a 24-hour application in Period 2 (Treatment B), the single application of 2 transdermal patch preparations each comprising 4 mg tizanidine for a period of 24 hours in Period 3 (Treatment C) and the single application of 1 transdermal patch preparation comprising 8 mg tizanidine (hereinafter also defined as "4TZT-b") for a period of 72 hours in Period 4 (Treatment D). The PK sampling for tizanidine was taken at pre-dose (before each oral administration or application of each patch preparation) and at 24 hours post-dose in Period 1, at 48 hours post-dose (from the start of the application of the patch preparation) in Periods 2 and 3, and at 96 hours post-dose (from the start of the application of the patch preparation) in Period 4. The adhesive strength and dermal irritancy of each preparation were measured in the study. There was a washout of at least 4 days between each treatment period (from the oral administration or from the start of the application of the patch preparation).

Treatments are described in Table 2 below.

TABLE 2

| Period | Dosage form | Concentration | Regimen |
|---|---|---|---|
| 1 | capsule (Zanaflex®) | 4 mg/capsule | 4 mg of 1 capsule single oral dose |
| 2 | dermal patch preparation (4TZT-a) | 4 mg/20 cm² thickness 150 μm | 4 mg of 1 patch preparation 24 hours application |
| 3 | dermal patch preparation (4TZT-a) | 4 mg/20 cm² thickness 150 μm | 4 mg of 2 patch preparations 24 hours application |
| 4 | dermal patch preparaion (4TZT-b) | 8 mg/20 cm² thickness 300 μm | 8 mg of 1 patch preparaion 72 hours application |

The patch preparations were applied to the intact skin on the upper arm.

Blood samples were collected at each sampling point shown in Table 3 below.

TABLE 3

| Period | Sampling point |
|---|---|
| 1 | 0 min, 10 min, 20 min, 30 min, 45 min, 1 hr, 1.25 hr, 1.5 hr, 1.75 hr, 2 hr, 2.5 hr, 3 hr, 4 hr, 5 hr, 6 hr, 7 hr, 8 hr, 24 hr |
| 2 | 0 hr, 2 hr, 4 hr, 6 hr, 8 hr, 10 hr, 12 hr, 16 hr, 20 hr, 24 hr, 28 hr, 32 hr, 36 hr, 40 hr, 48 hr |
| 3 | 0 hr, 2 hr, 4 hr, 6 hr, 8 hr, 10 hr, 12 hr, 16 hr, 20 hr, 24 hr, 28 hr, 32 hr, 36 hr, 40 hr, 48 hr |
| 4 | 0 hr, 2 hr, 4 hr, 6 hr, 8 hr, 10 hr, 12 hr, 16 hr, 20 hr, 24 hr, 36 hr, 48 hr, 60 hr, 72 hr, 76 hr, 80 hr, 84 hr, 88 hr, 96 hr |

Preparation of Dermal Patch Preparation

4TZT-a and 4TZT-b were prepared with the compositions of the above Preparation Example 1 according to the similar manner as described for I. Preparation of dermal patch preparation. The thickness of the adhesive layer in each preparation was adjusted to 150 μm or 300 μm.

Study Result

For all subjects, the blood samples for measuring tizanidine were collected in 4 ml blood collection tubes containing $D_2$EDTA at the scheduled time points shown in the above Table 3. Following the blood collection, the collected samples were centrifuged (approximately at 3000 rpm for 10 minutes) at ambient temperature as soon as possible. After the centrifugation, the resulting plasma samples were divided into 2 aliquots and sorted in suitably labeled tubes with 90 minutes of collection in a freezer at a temperature of −20±10° C. The samples were analyzed for plasma tizanidine with a validated bioanalytical method. The calculated pharmacokinetic parameters are shown in Table 4 below. The change in plasma concentrations (shown as geometric mean) of tizanidine observed in each treatment is shown in FIG. 1.

In addition to routine safety monitoring, daytime sleepiness, somnolence and sedation in subjects were assessed according to Stanford Sleepiness Scale (SSS). Specifically, a clinic staff asked the subjects to choose which number from SSS in Table 6 best describes their current level of alertness or sleepiness.

TABLE 4

| Phamacokinetic Parameter | 4 mg Zanaflex ® (Treatment A) Geometric Mean (Geom CV %) | n | 4TZT-a (24 hours) (Treatment B) Geometric Mean (Geom CV %) | n | 2 × 4TZT-a (24 hours) (Treatment C) Geometric Mean (Geom CV %) | n | 4TZT-b (72 hours) (Treatment D) Geometric Mean (Geom CV %) | n |
|---|---|---|---|---|---|---|---|---|
| AUC0-24 (ng*hr/mL) | . | . | 3.106 (286.6) | 15 | 10.20 (174.6) | 16 | 7.251 (162.0) | 15 |
| AUC0-72 (ng*hr/mL) | . | . | . | . | . | . | 33.69 (57.2) | 15 |
| AUC0-t (ng*hr/mL) | 7.030 (57.3) | 16 | 9.616 (89.2) | 15 | 23.13 (100.3) | 16 | 37.06 (53.7) | 15 |
| AUC0-inf (ng*hr/mL) | 7.341 (57.5) | 16 | 14.65 (54.1) | 11 | 21.43 (63.5) | 13 | 39.97 (55.0) | 11 |
| AUC % extrap (%) | 4.220 ± 1.8136 | 16 | 10.67 ± 5.4316 | 11 | 12.97 ± 8.7498 | 13 | 2.038 ± 1.7366 | 11 |
| Cmax (ng/mL) | 2.887 (54.2) | 16 | 0.5880 (145.6) | 15 | 1.449 (151.2) | 16 | 0.9548 (70.3) | 15 |
| Tmax (hr) | 0.9999 (0.747, 2.50) | 16 | 24.00 (20.0, 48.0) | 15 | 24.00 (16.0, 28.0) | 16 | 20.13 (20.0, 48.0) | 15 |
| Cavg (ng/mL) | . | . | 0.1294 (286.6) | 15 | 0.4252 (174.6) | 16 | 0.4680 (57.2) | 15 |
| Kel (1/hr) | 0.4520 ± 0.056736 | 16 | 0.06724 ± 0.017706 | 11 | 0.07055 ± 0.023515 | 13 | 0.1095 ± 0.047129 | 11 |
| T½ (hr) | 1.557 ± 0.19954 | 16 | 11.21 ± 3.8812 | 11 | 10.67 ± 2.8872 | 13 | 7.208 ± 2.3554 | 11 |

Treatment A: Single oral dose of 1 × 4 mg Zanaflex ® (tizanidine HCl) capsule
Treatment B: Single transdermal dose of 1 × 4 mg 4TZT-a patch preparation for 24 hours
Treatment C: Single transdermal dose of 2 × 4 mg (8 mg) 4TZT-a patch preparation for 24 hours
Treatment D: A single transdermal dose of 1 × 8 mg 4TZT-b patch preparation for 72 hours
. = Value missing or not reportable
Tmax is presented as median (minimum, maximum). AUC % extrap, Kel, and T½ are presented as Mean ± SD.
n = Number of observations
The data for a subject was excluded for Treatment D, because the predose concentration was >5% of Cmax.

Based on the data obtained from the single-dose study, the tizanidine plasma concentration was simulated in the multiple dose administration. The simulation results for 4 mg tizanidine oral capsule administered 3 times a day, 1 transdermal patch preparation comprising 8 mg tizanidine administered once every three days, and 1 transdermal patch preparation comprising 8 mg tizanidine administered once a day are shown in FIG. 6.

During the clinical study, a full physical examination was performed according to a predetermined procedure. No serious adverse event was reported during the study. Of the examination, the assessment about side effects such as somnolence and dizziness deserved notice. The expression rates of the side effects such as somnolence and dizziness in each treatment are shown in Table 5.

TABLE 5

| | Treatment | | | | |
|---|---|---|---|---|---|
| | A | B | C | D | Overall |
| Number of subject dosed | 16 | 16 | 16 | 16 | 16 |
| Nervous system disorder | 5 (31%) | 0 (0%) | 1 (6%) | 0 (0%) | 1 (6%) |
| Dizziness | 1 (6%) | 0 (0%) | 0 (0%) | 0 (0%) | 1 (6%) |
| Somnolence | 4 (25%) | 0 (0%) | 1 (6%) | 0 (0%) | 4 (25%) |

The expression rate of somnolence was markedly reduced in Treatments B to D, although somnolence is one of major adverse events due to the use of tizanidine.

TABLE 6

| Scale | |
|---|---|
| 1 | Feeling active, vital, alert, wide awake |
| 2 | Functioning at a high level but not at peak, able to concentrate |
| 3 | Relaxed, awake but not fully alert, responsive |
| 4 | A little foggy, let down |
| 5 | Foggy, beginning to lose track, difficulty staying awake |
| 6 | Sleepy, prefer to lie down, woozy |
| 7 | Almost in reverie, cannot stay awake, sleep onset appears imminent |

The results of each treatment are shown with the plasma concentration of tizanidine in FIG. 2 to FIG. 5.

II. Multiple-Dose Pharmacokinetic Study:

This study was a comparative, multiple-dose, fixed-sequence, 2-period, 3-treatment, pharmacokinetic, and pharmacodynamic study of the transdermal patch preparation comprising 8 mg of tizanidine. 30 healthy adult male and female subjects were included in the study. In Period 1, all 30 subjects received the multiple oral dose of 2 mg or 4 mg tizanidine capsule administered twice a day with a 4-hour interval between doses at 4 mg/day on Day 1 then increasing to 8 mg/day on Day 2 and 16 mg/day on Day 3 (reference regimen). In Period 2, the subjects who completed Period 1 were randomized to conduct one of the 2 test regimens, either the application of 1 transdermal patch preparation comprising 8 mg tizanidine applied every 24 hours for 7 days or the application of 2 transdermal patch preparations each comprising 8 mg tizanidine applied every 24 hours for 7 days (test regimens). There was a washout period of at least 5 days between study drug administration in Period 1 (from the first oral dose in the morning on Day 3) and first study drug administration in Period 2 (from the start of the first application of patch preparation).

Treatments are described in Table 7 below.

TABLE 7

|  | 4 mg Zanaflex® (Treatment Am) | 8 mg 4TZT-a (Treatment Bm) | 2*8 mg 4TZT-b (Treatment Cm) |
|---|---|---|---|
| Pharmacokinetic Parameter | Geometric Mean | Geometric Mean | Geometric Mean |
| $C_{ss,max}$ (ng/mL) | — | 0.45 | 0.82 |
| $C_{ss,min}$ (ng/mL) | — | 0.22 | 0.40 |
| Cavg | — | 0.33 | 0.61 |
| Kel (1/hr) | 0.391 | 0.059 | 0.056 |
| T1/2 (hr) | 1.8 | 11.8 | 12.5 |
| { $C_{ss}$ (max)-$C_{ss}$ (min) }/$C_{ss}$ (max) | — | 0.51 | 0.51 |

Treatment Am:
(reference regimen)-Multiple oral doses given as 4 mg/day on Day 1 then increasing to 8 mg/day on Day 2 and 16 mg/day on Day 3 of tizanidine capsules (1 × 2 mg then 1 × 4 mg and 2 × 4 mg tizanidine HCl capsules; Acorda Zanaflex®) given twice a day with a 4-hour interval between doses.
Treatment Bm:
(test regimen 1)-Multiple transdermal 8 mg doses of 1 patch preparation × 4TZT-b (8 mg) following a 24-hour application for 7 days on Days 1 to 7.
Treatment Cm:
(test regimen 2)-Multiple transdermal 16 mg doses of 2 patch preparations × 4TZT-b (8 mg) following a 24-hour application for 7 days on Days 1 to 7.

The patch preparations were applied to the intact skin on the middle back at Hour 0 on the morning of Days 1 to 7.

PK sampling for tizanidine was taken at pre-dose (before each oral administration or application of each patch preparation); at 4 hours following the dose in the morning on Day 2 of Period 1; at 24 hours following the doses in the morning on Day 3 of Period 1 and Day 1 of Period 2; and at 48 hours following the application of patch preparation on Day 7 of Period 2.

The PD assessments (computerized cognitive function testing and sedation testing) were performed prior to and at 6 hours following each first oral dose in the morning on Days 2 and 3 in Period 1, and prior to and at 24 hours following each application of patch preparations on Days 1 and 7 in Period 2. The adhesive strength and dermal irritancy of each preparation were measured in the study.

Preparation of Dermal Patch Preparation

The patch preparations were prepared according to the similar manner as described for I. Preparation of dermal patch preparation.

Study Result

For all subjects, the blood samples for measuring tizanidine were collected in 4 ml blood collection tubes containing $D_2EDTA$ at scheduled time points. Following the blood collection, the collected samples were centrifuged (approximately at 3000 rpm for 10 minutes) at ambient temperature as soon as possible. After the centrifugation, the resulting plasma samples were divided into 2 aliquots and sorted in suitably labeled tubes with 90 minutes of collection in a freezer at a temperature of −20±10° C. The samples were analyzed for plasma tizanidine with a validated bioanalytical method. The calculated pharmacokinetic parameters for multiple-dose pharmacokinetic study are shown in Table 7 below. The change in plasma concentrations (shown as geometric mean) of tizanidine observed in each treatment in the multiple dose pharmacokinetic study is shown in FIG. 7.

The following values (Mean and SD values of tizanidine residual concentration (%)) were obtained from a population of 12 subjects, over 7 days with 1 patch preparation.

TABLE 8

| Treatment B (1 patch preparation) (N = 12) | | | | | | | |
|---|---|---|---|---|---|---|---|
| | Residual conc. of tizanidine (%) | | | | | | |
| | Day 1 | Day 2 | Day 3 | Day 4 | Day 5 | Day 6 | Day 7 |
| Subject No. | 1 | 65 | | 82 | | | 71 | 78 |
| | 4 | 69 | | | | | 66 | 67 |
| | 6 | 66 | | | | | 76 | 79 |
| | 8 | 54 | | 64 | | | 69 | 60 |
| | 10 | 73 | | | | | 69 | 72 |
| | 12 | 75 | | | | | 76 | 71 |
| | 13 | 66 | | | | | 61 | 59 |
| | 15 | 63 | | | 68 | 60 | 65 | 61 |
| | 17 | 93 | | | | | 59 | 68 |
| | 20 | 71 | | 76 | 68 | | 72 | 74 |
| | 21 | 86 | 107 | 75 | | | 66 | 76 |
| | 24 | 94 | | | | | 76 | 79 |
| Mean | | 72.7 | | | | | 68.8 | 70.2 |
| SD | | 12.3 | | | | | 5.6 | 7.4 |

The following values (Mean and SD values of tizanidine residual amount (mg)) were obtained from a population of 12 subjects, over 7 days with 1 patch preparation.

TABLE 9

| Treatment B (1 patch preparation) (N = 12) | | | | | | | |
|---|---|---|---|---|---|---|---|
| | Residual amount of tizanidine (mg) | | | | | | |
| | Day 1 | Day 2 | Day 3 | Day 4 | Day 5 | Day 6 | Day 7 |
| Subject No. | 1 | 5.2 | | 6.6 | | | 5.6 | 6.3 |
| | 4 | 5.5 | | | | | 5.3 | 5.3 |
| | 6 | 5.3 | | | | | 6.1 | 6.3 |
| | 8 | 4.3 | | 5.1 | | | 5.5 | 4.8 |
| | 10 | 5.8 | | | | | 5.5 | 5.7 |
| | 12 | 6.0 | | | | | 6.1 | 5.7 |
| | 13 | 5.3 | | | | | 4.9 | 4.7 |
| | 15 | 5.0 | | | 5.5 | 4.8 | 5.2 | 4.9 |
| | 17 | 7.4 | | | | | 4.8 | 5.4 |
| | 20 | 5.6 | | 6.1 | 5.5 | | 5.7 | 5.9 |
| | 21 | 6.8 | 8.5 | 6.0 | | | 5.2 | 6.0 |
| | 24 | 7.5 | | | | | 6.1 | 6.3 |
| Mean | | 5.8 | | | | | 5.5 | 5.6 |
| SD | | 1.0 | | | | | 0.4 | 0.6 |

The following values (Mean and SD values of tizanidine residual concentration (%)) were obtained from a population of 12 subjects, over 7 days with 2 patch preparations.

TABLE 10

| Treatment C (2 patch preparations) (N = 12) | | | | | | | |
|---|---|---|---|---|---|---|---|
| | Residual conc. of Tizanidine (%) | | | | | | |
| | Day 1 | Day 2 | Day 3 | Day 4 | Day 5 | Day 6 | Day 7 |
| subject No. | 2 | 69 | | | | | 69 | 69 |
| | 3 | 72 | | | | | 72 | 69 |
| | 5 | 70 | 75 | | | | 73 | 74 |
| | 7 | 69 | | | | 72 | 74 | 70 |
| | 9 | 77 | | | 74 | | 72 | 78 |
| | 11 | 64 | | | 65 | | 64 | 65 |
| | 14 | 69 | | | 70 | | 71 | 64 |
| | 16 | 68 | | | | | 57 | 77 |
| | 18 | 84 | | | 81 | | 82 | 93 |

TABLE 10-continued

Treatment C (2 patch preparations) (N = 12)

Residual conc. of Tizanidine (%)

|  |  | Day 1 | Day 2 | Day 3 | Day 4 | Day 5 | Day 6 | Day 7 |
|---|---|---|---|---|---|---|---|---|
|  | 19 | 73 | 85 |  |  |  | 74 | 75 |
|  | 22 | 82 |  | 75 |  |  | 71 | 73 |
|  | 23 | 81 |  | 72 |  |  | 76 | 75 |
| Mean |  | 72.9 |  |  |  |  | 71.2 | 73.6 |
| SD |  | 6.4 |  |  |  |  | 6.1 | 7.5 |

The following values (Mean and SD values of tizanidine residual amount (mg)) were obtained from a population of 12 subjects, over 7 days with 2 patch preparations.

TABLE 11

Treatment C (2 patch preparations) (N = 12)

Residual amount of Tizanidine (mg)

|  |  | Day 1 | Day 2 | Day 3 | Day 4 | Day 5 | Day 6 | Day 7 |
|---|---|---|---|---|---|---|---|---|
| Subject | 2 | 11.0 |  |  |  |  | 11.0 | 11.0 |
| No. | 3 | 11.5 |  |  |  |  | 11.5 | 11.0 |
|  | 5 | 11.2 | 12.1 |  |  |  | 11.7 | 11.9 |
|  | 7 | 11.0 |  |  |  | 11.5 | 11.8 | 11.2 |
|  | 9 | 12.3 |  |  | 11.8 |  | 11.5 | 12.5 |
|  | 11 | 10.2 |  | 10.4 |  |  | 10.3 | 10.4 |
|  | 14 | 11.0 |  |  | 11.3 |  | 11.4 | 10.2 |
|  | 16 | 10.8 |  |  |  |  | 9.1 | 12.4 |
|  | 18 | 13.4 |  |  | 13.0 |  | 13.1 | 14.8 |
|  | 19 | 11.6 | 13.7 |  |  |  | 11.8 | 12.0 |
|  | 22 | 13.1 |  | 12.0 |  |  | 11.3 | 11.7 |
|  | 23 | 13.0 |  | 11.5 |  |  | 12.1 | 12.0 |
| Mean |  | 11.7 |  |  |  |  | 11.4 | 11.8 |
| SD |  | 1.0 |  |  |  |  | 1.0 | 1.2 |

III. Tizanidine Transdermal System
A. Description of Tizanidine Transdermal System
PStructure of Patch Prepration As shown in FIG. 8, the tizanidine transdermal system is a rectangular-shaped patch preparation consisting of 1) a backing layer, 2) an overlaying adhesive layer containing no drug, 3) a separating layer, 4) a drug adhesive matrix and 5) a release liner. As shown in FIGS. 9 and 10, the release liner has a slit on the overlay area, that is, a design that enables the patch preparation to be applied to the skin without touching the drug adhesive matrix. The drug adhesive matrix contains 0.46 mg/cm$^2$ to about 0.8 mg/cm$^2$ of tizanidine hydrochloride as the drug (0.46 mg/cm$^2$ equivalent to about 0.40 mg/cm$^2$ tizanidine base). 1 patch preparation is packaged in a polyethylene aluminum-laminated pouch.

TABLE 12

Table 12: Size of patch preparation

|  | Patch Preparation (1) | Patch Preparation (2) | Patch Preparation (3) | Patch Preparation (4) |
|---|---|---|---|---|
| Drug Matrix Area | 20 cm$^2$ (40 × 50 mm) | 40 cm$^2$ (55 × 73 mm) | 80 cm$^2$ (70 × 115 mm) | 120 cm$^2$ (85 × 140 mm) |
| Overlay Area | 36 cm$^2$ (55 × 65 mm) | 62 cm$^2$ (70 × 88 mm) | 110 cm$^2$ (85 × 130 mm) | 155 cm$^2$ (100 × 155 mm) |
| Tizanidine content | 8 mg | 16 mg | 32 mg | 48 mg |

TABLE 13

Table 13: Thickness of adhesive

|  | Wet | Dry |
|---|---|---|
| Drug Matrix Area | about 600 μm (380 g/m$^2$) | about 300 μm (267 g/m$^2$) |
| Overlay Area | about 300 μm (180 g/m$^2$) | about 120 μm (90 g/m$^2$) |

B. One Example of Preparation

|  | Ingredient | Concentration (w/w %) | Batch formula (10 kg scale) Amount per batch (g) |
|---|---|---|---|
| Drug Adhesive Area | Drug Adhesive Matrix | | |
|  | Tizanidine HCl | 1.72 | 172 |
|  | Oleic Acid | 1.50 | 150 |
|  | Potassium Sorbate | 0.89 | 89 |
|  | Sorbic acid | 0.66 | 66 |
|  | Sodium Sulfite | 0.10 | 10 |
|  | Propyl Gallate | 0.05 | 5 |
|  | Purified Water | 0.50 | 50 |
|  | Concentrated Glycerin | 5.00 | 500 |
|  | Propylene Glycol | 8.00 | 1000 |
|  | Butylene Glycol | 3.00 | 375 |
|  | Oleyl Alcohol | 10.00 | 1000 |
|  | Colloidal Silicon Dioxide | 3.00 | 300 |
|  | Mineral Oil | 21.58 | 2158 |
|  | Terpene Resin | 28.00 | 2800 |
|  | Styrene-Isoprene-Styrene Block Copolymer | 16.00 | 1600 |
|  | Ethyl Acetate [1] | (40) | 4000 |
|  | Total Weight of Drug Adhesive Matrix | 100.00 | 14275 |
|  | Separating Layer | | |
|  | Non-woven PET Cloth | — | — |
| Overlay Area | Overlaying Adhesive Layer | | |
|  | DURO-TAK 387-2287 | 89 | 17800 |
|  | Propylene Glycol | 8 | 1200 |
|  | Butylene Glycol | 3 | 450 |
|  | Total Weight of overlaying adhesive layer | 100 | 19450 |
|  | Backing Layer/Release Liner | | |
|  | Non-woven PET Cloth | — | — |
|  | Release Liner | — | — |

[1] Ethyl acetate is removed during manufacturing process.

IV. Manufacturing Process of Tizanidine Transdermal System

The tizanidine transdermal system can be manufactured in the following manner, but is not limited thereto.
a) Manufacturing process of drug adhesive matrix roll
   (i) Dissolving of active ingredient (API)
      Tizanidine hydrochloride and solvents were mixed and dissolved.
   (ii) Dissolving of adhesive
      Adhesives were dissolved in ethyl acetate.
   (iii) Mixing of adhesive solutions
      The above (i) and (ii) were homogeneously mixed and stirred.
   (iv) Coating/Drying/Laminating
      The resulting mixture is coated/laminated on the release liner and dried. The release liner/drug adhesive matrix (dried paste) and non-woven backing (separating layer) were laminated.
b) Manufacturing process of overlaying roll
   (i) Mixing of adhesive solution DURO-ATK and solvents were mixed.
   (ii) Coating/Drying/Laminating
      The resulting mixture was coated on the release liner and dried. The release liner/adhesive and non-woven backing (overlay backing) are laminated.
c) Manufacturing process of tizanidine transdermal system
   (i) Converting: Multi-layer laminating/Cutting
      Multi-layer lamination of the laminate roll of drug adhesive matrix (a) and overlay (b) and then cutting
   (ii) Packaging
      The patch preparations were packaged into aluminum-laminated pouches.

ENUMERATED EMBODIMENTS

Specific enumerated embodiments [001] to [111] provided below are for illustration purposes only, and do not otherwise limit the scope of the disclosed subject matter, as defined by the claims. These enumerated embodiments encompass all combinations, sub-combinations, and multiple referenced (e.g., multiple dependent) combinations described therein.

[1] A method of administering a transdermal patch preparation comprising tizanidine or a pharmaceutically acceptable salt thereof to a subject in need thereof, wherein the transdermal patch preparation releases about 6 mg to about 36 mg of tizanidine or a pharmaceutically acceptable salt thereof for at least about 24 hours.

[2] A method of administering a transdermal patch preparation comprising tizanidine or a pharmaceutically acceptable salt thereof to a subject in need thereof, wherein the transdermal patch preparation releases about 4 mg to about 36 mg of tizanidine or a pharmaceutically acceptable salt thereof for at least about 24 hours.

[3] The method of the embodiment [1] or [2], wherein the tizanidine or pharmaceutically acceptable salt thereof is located in the composition of the adhesive layer of the transdermal patch preparation.

[4] The method of the embodiment [1] or [2], wherein the transdermal patch preparation comprises tizanidine or a pharmaceutically acceptable salt thereof and a sorbate component selected from the group consisting of sorbic acid, sodium sorbate, potassium sorbate, calcium sorbate and a combination thereof.

[5] The method of the embodiment [4], wherein the tizanidine or a pharmaceutically acceptable salt thereof and the sorbate component are each independently located in the composition of the adhesive layer of the transdermal patch preparation.

[6] The method of the embodiment [4] or [5], wherein the molar ratio of the sorbate component to tizanidine or a pharmaceutically acceptable salt thereof is about 0.5 to 3.0.

[7] The method of any one of embodiments [4] or [5], wherein the molar ratio of the sorbate component to tizanidine or a pharmaceutically acceptable salt thereof is about 2.2 to 2.8.

[8] The method of any one of the embodiments [1] to [7], wherein the tizanidine or pharmaceutically acceptable salt thereof has a single dose $T_{max}$ of at least about 12 hours.

[9] The method of any one of the embodiments [1] to [7], wherein the tizanidine or pharmaceutically acceptable salt thereof has a single dose $T_{max}$ of up to about 48 hours.

[10] The method of any one of the embodiments [1] to [7], wherein the tizanidine or pharmaceutically acceptable salt thereof has a single dose $T_{max}$ of about 12 to about 48 hours.

[11] The method of any one of the embodiments [1] to [7], wherein the tizanidine or pharmaceutically acceptable salt thereof has a single dose $T_{max}$ of about 24 hours.

[12] The method of any one of the embodiments [1] to [11], wherein the multiple-dose administration to a human subject provides a plasma concentration profile in steady state satisfying the following formula:

$$\frac{(Css, \max - Css, \min)}{Css, \max} < 0.9.$$

[13] The method of the embodiment [12], wherein $C_{ss,max}$ is about 0.01 ng/mL to about 0.5 ng/mL per mg of tizanidine a day.

[14] The method of the embodiment [12], wherein the $C_{ss,max}$ is about 0.01 ng/mL to about 0.3 ng/mL per mg of tizanidine a day.

[15] The method of any one of the embodiments [1] to [14], wherein the tizanidine has an elimination rate constant of about 0.01 to about 0.2 $h^{-1}$.

[16] The method of any one of the embodiments [1] to [14], wherein the tizanidine has an elimination rate constant of about 0.01 to about 0.2 $h^{-1}$, calculated from the elimination time in the transdermal patch preparation.

[17] The method of any one of the embodiments [1] to [16], wherein the single-dose administration to a human subject provides an $AUC_{0-inf}$ of at least 1.0 ng*h/mL per mg of tizanidine.

[18] The method of any one of the embodiments [1] to [17], wherein the subject is suffering from a disease or disorder ameliorated with tizanidine or a pharmaceutically acceptable salt thereof.

[19] The method of any one of the embodiments [1] to [17], wherein the subject is suffering from spasticity.

[20] The method of any one of the embodiments [1] to [19], wherein the transdermal patch preparation has a surface area of at least about 10 $cm^2$.

[21] The method of any one of the embodiments [1] to [20], wherein the transdermal patch preparation has a surface area of up to about 200 $cm^2$.

[22] The method of any one of the embodiments [1] to [21], wherein the transdermal patch preparation has a surface area of about 10 $cm^2$ to about 200 $cm^2$.

[23] The method of any one of the embodiments [1] to [22], wherein the transdermal patch preparation comprises tizanidine or a pharmaceutically acceptable salt thereof and at least one of:

sorbate component selected from sorbic acid and/or a metal salt of sorbic acid,
saturated or unsaturated $C_{4-20}$ aliphatic acid,
monovalent alcohol,
trivalent alcohol,
divalent alcohol,
filler,
softener,
tackifier resin,
rubber polymer,
inorganic basic compound, and
antioxidant.

[24] The method of any one of the embodiments [1]-[22], wherein the transdermal patch preparation comprises in the composition of the adhesive layer tizanidine or a pharmaceutically acceptable salt thereof, sorbate component selected from sorbic acid and/or a metal salt of sorbic acid, and at least one of:
saturated or unsaturated $C_{4-20}$ aliphatic acid,
monovalent alcohol,
trivalent alcohol,
divalent alcohol,
filler,
softener,
tackifier resin,
rubber polymer,
inorganic basic compound, and
antioxidant.

[25] The method of any one of the embodiments [1] to [22], wherein the transdermal patch preparation comprises in the composition of the adhesive layer:
tizanidine or a pharmaceutically acceptable salt thereof,
sorbate component selected from sorbic acid and/or a metal salt of sorbic acid,
saturated or unsaturated $C_{4-20}$ aliphatic acid,
monovalent alcohol,
trivalent alcohol,
divalent alcohol,
filler,
softener,
tackifier resin,
rubber polymer,
inorganic basic compound, and
antioxidant.

[26] The method of any one of the embodiments [22] to [25], wherein each of the ingredients in the transdermal patch preparation is independently located in the adhesive layer composition.

[27] The method of any one of the embodiments [1] to [26], wherein the transdermal patch preparation comprises one or more basic components selected from an organic basic compound, an inorganic basic compound, a salt of strong base, or a combination thereof.

[28] The method of the embodiment [27], wherein the organic basic compound comprises $C_{2-9}$ alkanolamine.

[29] The method of the embodiment [28], wherein the $C_{2-9}$ alkanolamine is selected from monoethanolamine, monoisopropanolamine, diethanolamine, diisopropanolamine, triethanolamine, triisopropanolamine, ethylenediamine, trishydroxymethylaminomethane (trometamol), or a combination thereof.

[30] The method of the embodiment [27], wherein the organic basic compound comprises a basic amino acid.

[31] The method of the embodiment [30], wherein the basic amino acid is arginine.

[32] The method of the embodiment [27], wherein the organic basic compound comprises an organic amine compound having three hydroxyl groups in the molecule.

[33] The method of the embodiment [32], wherein the organic amine compound having three hydroxyl groups in the molecule is selected from triethanolamine, triisopropanolamine, trishydroxymethylaminomethane, or a combination thereof.

[34] The method of the embodiment [27], wherein the inorganic basic compound comprises a compound containing an alkali metal, an alkali earth metal, or a combination thereof.

[35] The method of the embodiment [27], wherein the inorganic basic compound comprises a basic compound containing hydroxyl group in the molecule.

[36] The method of the embodiment [35], wherein the basic compound containing hydroxyl group in the molecule is selected from sodium hydroxide, potassium hydroxide, calcium hydroxide, or a combination thereof.

[37] The method of the embodiment [27], wherein the salt of strong base comprises a metal salt of carboxylic acid.

[38] The method of the embodiment [37], wherein the metal salt of carboxylic acid is selected from sodium benzoate, sodium propionate, calcium propionate, sodium fumarate, sodium sorbate, potassium sorbate, or a combination thereof.

[39] The method of the embodiment [27], wherein the salt of strong base comprises a metal salt of hydroxyl acid.

[40] The method of the embodiment [39], wherein the metal salt of hydroxyl acid is selected from sodium lactate, sodium tartrate, potassium tartrate, sodium citrate, or a combination thereof.

[41] The method of any one of the embodiments [1] to [40], wherein the transdermal patch preparation comprises one or more basic components and one or more sorbate components such that the basic component is comprised in a concentration of about 0.4 mol to about 3.0 mol per mol of sorbate component.

[42] The method of any one of the embodiments [1] to [40], wherein the transdermal patch preparation comprises one or more basic components and one or more sorbate components such that the basic component is comprised in a concentration of about 0.5 mol to about 2.5 mol per mol of sorbate component.

[43] The method of any one of the embodiments [1] to [40], wherein the transdermal patch preparation comprises one or more basic components and one or more sorbate components such that the basic component is comprised in a concentration of about 0.5 mol to about 2.0 mol per mol of sorbate component.

[44] The method of any one of the embodiments [1] to [40], wherein the transdermal patch preparation comprises one or more basic components and one or more sorbate components such that the basic component is comprised in a concentration of about 0.5 mol to about 1.6 mol per mol of sorbate component.

[45] The method of any one of the embodiments [1] to [44], wherein the transdermal patch preparation comprises one or more compounds for effectively dissolving each of tizanidine or pharmaceutically acceptable salt thereof and a sorbate component.

[46] The method of any one of the embodiments [1] to [44], wherein the transdermal patch preparation comprises one or more compounds for effectively dissolving each of tizanidine or a pharmaceutically acceptable salt thereof and a sorbate component, such that tizanidine or pharmaceutically acceptable salt thereof effectively produces a percutaneous absorption accelerating effect.

[47] The method of any one of the embodiments [40] to [46], wherein the compound is a percutaneous absorption accelerator.

[48] The method of the embodiment [47], wherein the percutaneous absorption accelerator comprises one or more saturated or unsaturated $C_{4-20}$ aliphatic acids, excluding ascorbic acid.

[49] The method of the embodiment [48], wherein the saturated or unsaturated $C_{4-20}$ aliphatic acid comprises levulinic acid, capric acid, lauric acid, myristic acid, palmitic acid, stearic acid, isostearic acid, oleic acid, or a combination thereof.

[50] The method of any one of the embodiments [47] to [49], wherein the percutaneous absorption accelerator is comprised in the preparation, such that the total concentration of the sorbate component and the percutaneous absorption accelerator is about 0.8 mol to about 2.5 mol per mol of the basic component.

[51] The method of any one of the embodiments [47] to [49], wherein the percutaneous absorption accelerator is comprised in the preparation, such that the total concentration of the sorbate component and the percutaneous absorption accelerator is about 0.8 mol to about 2.0 mol per mol of the basic component.

[52] The method of any one of the embodiments [47] to [49], wherein the percutaneous absorption accelerator is comprised in the preparation, such that the total weight of the sorbate component and the percutaneous absorption accelerator is about 2.0 wt % to about 3.0 wt % of the total weight of the adhesive layer.

[53] The method of any one of the embodiments [47] to [49], wherein the percutaneous absorption accelerator is comprised in the preparation, such that the total weight of the sorbate component and the percutaneous absorption accelerator is about 2.0 wt % to about 2.5 wt % of the total weight of the adhesive layer.

[54] The method of any one of the embodiments [1] to [53], wherein the transdermal patch preparation comprises an alcohol having one or more hydroxyl groups in the molecule.

[55] The method of the embodiment [54], wherein the alcohol comprises a monovalent alcohol.

[56] The method of the embodiment [54], wherein the alcohol is selected from lauryl alcohol, myristyl alcohol, oleyl alcohol, isostearyl alcohol, cetyl alcohol, or a combination thereof.

[57] The method of the embodiment [54], wherein the alcohol comprises a divalent alcohol selected from propylene glycol, butylene glycol, dipropylene glycol, diisobutylene glycol, polyethylene glycol, hexylene glycol, or a combination thereof.

[58] The method of the embodiment [54], wherein the alcohol is selected from glycerin, hexanetriol, or a combination thereof.

[59] The method of any one of the embodiments [1] to [58], wherein the transdermal patch preparation comprises an ester compound.

[60] The method of the embodiment [59], wherein the ester compound is selected from diethyl sebacate, methyl laurate, diisopropyl adipate, isopropyl myristate, medium-chain fatty acid triglyceride, or a combination thereof.

[61] The method of the embodiment [60], wherein the medium-chain fatty acid triglyceride is triglyceride having $C_{6-12}$ fatty acid chain.

[62] The method of any one of the embodiments [1] to [61], wherein the transdermal patch preparation comprises an amide compound.

[63] The method of the embodiment [62], wherein the amide compound comprises lauric acid diethanolamide.

[64] The method of any one of the embodiments [1] to [63], wherein the transdermal patch preparation comprises a matrix type plaster.

[65] The method of the embodiment [64], wherein the matrix type plaster is prepared by dispersing a composition into an adhesive layer comprising a polymer.

[66] The method of the embodiment [64], wherein the composition comprises the ingredients in the adhesive layer composition of any one of the embodiments [1] to [63].

[67] The method of the embodiment [64], wherein the composition is described in the adhesive layer composition of any one of the embodiments [1] to [63].

[68] The method of any one of the embodiments [65] to [67], wherein the polymer comprises an acrylic polymer, a rubber polymer, a silicone polymer, a vinyl ester-based polymer, or a combination thereof.

[69] The method of any one of the embodiments [65] to [67], wherein the polymer comprises a rubber polymer selected from styrene-isoprene-styrene block copolymer, styrene-butadiene-styrene block copolymer, polyisoprene, polyisobutylene, polybutadiene, or a combination thereof.

[70] The method of any one of the embodiment [68] or [69], wherein the polymer comprises a rubber polymer and the concentration of the rubber polymer is about 5 wt % to about 40 wt % of the dried adhesive layer.

[71] The method of any one of the embodiment [68] or [69], wherein the polymer comprises a rubber polymer and the concentration of the rubber polymer is about 10 wt % to about 30 wt % of the dried adhesive layer.

[72] The method of any one of the embodiment [68] or [69], wherein the polymer comprises a rubber polymer and the concentration of the rubber polymer is about 15 wt % to about 25 wt % of the dried adhesive layer.

[73] The method of the embodiment [68], wherein the concentration of the acrylic polymer is about 45 wt % to about 95 wt % of the total weight of the dried adhesive layer.

[74] The method of the embodiment [68], wherein the concentration of the acrylic polymer is about 50 wt % to about 90 wt % of the total weight of the dried adhesive layer.

[75] The method of the embodiment [68], wherein the concentration of the silicone polymer is about 45 wt % to about 95 wt % of the total weight of the dried adhesive layer.

[76] The method of the embodiment [68], wherein the concentration of the silicone polymer is about 50 wt % to about 90 wt % of the total weight of the dried adhesive layer.

[77] The method of any one of the embodiments [64] to [76], wherein the transdermal patch preparation comprises an adhesive layer that comprises a filler.

[78] The method of any one of the embodiments [64] to [76], wherein the transdermal patch preparation comprises a filler in a concentration of about 0.5 wt % to about 5 wt % of the total weight of the adhesive layer.

[79] The method of the embodiment [78], wherein the filler is selected from hydrous silica, fumed silica, crystalline cellulose, starch, carmellose, a metal salt of carmellose, or a combination thereof.

[80] The method of any one of the embodiments [64] to [79], wherein the transdermal patch preparation comprises a tackifier resin, a softener, an antioxidant, or a combination thereof.

[81] The method of the embodiment [80], wherein the tackifier resin is selected from rosin ester, hydrogenated rosin ester, rosin maleate, alicyclic saturated hydrocarbon resin, terpene resin, polyolefin resin, or a combination thereof.

[82] The method of the embodiment [80], wherein the softener is selected from naphthenic processing oil, vegetable oil, liquid rubber, liquid paraffin, or a combination thereof.

[83] The method of the embodiment [82], wherein the vegetable oil is selected from *camellia* oil, castor oil, or a combination thereof.

[84] The method of the embodiment [82], wherein the liquid rubber is selected from liquid polybutene, liquid isoprene rubber, or a combination thereof.

[85] The method of the embodiment [80], wherein the antioxidant is selected from dibutylhydroxytoluene, ascorbic acid, propyl gallate, sodium sulfite, sodium pyrosulfite, or a combination thereof.

[86] The method of any one of the embodiments [1] to [85], wherein the transdermal patch preparation comprises a non-aqueous adhesive layer composition.

[87] The method of any one of the embodiments [1] to [85], wherein the transdermal patch preparation comprises a non-aqueous adhesive layer composition containing less than about 3.0 wt % of water.

[88] The method of any one of the embodiments [1] to [85], wherein the transdermal patch preparation comprises a non-aqueous adhesive layer composition containing less than about 1.0 wt % of water.

[89] The method of any one of the embodiments [1] to [85], wherein each of the ingredients in the transdermal patch preparation is independently located in the composition of the adhesive layer.

[90] The method of any one of the embodiments [1] to [85], wherein one or more of the following:
  tizanidine or a pharmaceutically acceptable salt thereof,
  a sorbate component,
  a basic component,
  a compound for effectively dissolving each of tizanidine or a pharmaceutically acceptable salt thereof and
  a sorbate component,
  a percutaneous absorption accelerator,
  an alcohol,
  an ester compound,
  an amide compound,
  a polymer,
  a filler,
  a tackifier resin,
  a softener, and
  an antioxidant,
when present, are independently located in the adhesive layer composition.

[91] The method of any one of the embodiments [1] to [85], wherein each of the following:
  tizanidine or a pharmaceutically acceptable salt thereof,
  a sorbate component,
  a basic component,
  a compound for effectively dissolving each of tizanidine or pharmaceutically acceptable salt thereof and
  a sorbate component,
  a percutaneous absorption accelerator,
  an alcohol,
  an ester compound,
  an amide compound,
  a polymer,
  a filler,
  a tackifier resin,
  a softener, and
  an antioxidant,
when present, is independently located in the adhesive layer composition.

[92] The method of any one of embodiments [1] to [91], wherein the adhesive layer composition is substantially uniformly dispersed.

[93] The method of any one of embodiments [1] to [92], wherein the frequency of administration is 1 transdermal patch preparation per day.

[94] The method of any one of the embodiments [1] to [92], wherein the frequency of administration is 2 transdermal patch preparations per day.

[95] The method of any one of the embodiments [1] to [92], wherein the frequency of administration is 1 transdermal patch preparation every 2 days.

[96] The method of any one of the embodiments [1] to [92], wherein the frequency of administration is 1 transdermal patch preparation every 3 days.

[97] The method of any one of the embodiments [1] to [92], wherein the frequency of administration is 1 transdermal patch preparation every 4 days.

[98] The method of any one of the embodiments [1] to [92], wherein the frequency of administration is 1 transdermal patch preparation every 5 days.

[99] The method of any one of the embodiments [1] to [92], wherein the frequency of administration is 1 transdermal patch preparation every 6 days.

[100] The method of any one of the embodiments [1] to [92], wherein the frequency of administration is 1 transdermal patch preparation every 7 days.

[101] The method of any one of the embodiments [1] to [92], wherein the frequency of administration is 1 transdermal patch preparation every 1 to 7 days.

[102] The method of any one of the embodiments [93] to [101], wherein the adhesion time of the transdermal patch preparation to the skin is about 12 hours.

[103] The method of any one of the embodiments [93] to [101], wherein the adhesion time of the transdermal patch preparation to the skin is about 24 hours.

[104] The method of any one of the embodiments [93] to [101], wherein the adhesion time of the transdermal patch preparation to the skin is about 2 days.

[105] The method of any one of the embodiments [93] to [101], wherein the adhesion time of the transdermal patch preparation to the skin is about 3 days.

[106] The method of any one of the embodiments [93] to [101], wherein the adhesion time of the transdermal patch preparation to the skin is about 4 days.

[107] The method of any one of the embodiments [93] to [101], wherein the adhesion time of the transdermal patch preparation to the skin is about 5 days.

[108] The method of any one of the embodiments [93] to [101], wherein the adhesion time of the transdermal patch preparation to the skin is about 6 days.

[109] The method of any one of the embodiments [93] to [101], wherein the adhesion time of the transdermal patch preparation to the skin is about 7 days.

[110] The method of any one of the embodiments [93] to [101], wherein the adhesion time of the transdermal patch preparation to the skin is continuous.

[111] The method of any one of the embodiments [93] to [101], wherein the adhesion time of the transdermal patch preparation to the skin is not continuous.

The invention claimed is:

1. A method of systemically delivering tizanidine to treat a musculoskeletal disease or disorder, comprising:
    administering a transdermal patch preparation comprising tizanidine or a pharmaceutically acceptable salt thereof to a subject in need thereof, and
    releasing about 4 mg to about 36 mg of tizanidine or a pharmaceutically acceptable salt thereof for at least about 24 hours.

2. The method of claim 1, wherein an elimination rate constant of tizanidine is about 0.01 to about 0.2 $h^{-1}$.

3. The method of claim 1, wherein the transdermal patch preparation has an $AUC_{0-inf}$ of at least 1.0 ng*h/mL per mg of tizanidine.

4. The method of claim 1 for treating spasticity.

5. The method of claim 1, wherein the transdermal patch preparation further comprises a sorbate component selected from the group consisting of sorbic acid, sodium sorbate, potassium sorbate, calcium sorbate, and a combination thereof.

6. The method of claim 1, wherein the transdermal patch preparation provides a single dose $T_{max}$ of about 12 to about 48 hours.

7. The method of claim 1, wherein the multiple-dose administration to a human subject provides a plasma concentration profile in steady state satisfying the following formula:

$$\frac{(Css, \max - Css, \min)}{Css, \max} < 0.9.$$

8. The method of claim 1, wherein the transdermal patch preparation provides a $C_{ss,max}$ of about 0.01 ng/mL to about 0.5 ng/mL per mg of tizanidine a day.

9. The method of claim 1, wherein the transdermal patch preparation provides an elimination rate constant of tizanidine of about 0.01 to about 0.2 $h^{-1}$, calculated from the elimination time of the transdermal patch preparation.

10. The method of claim 1, wherein the subject is suffering from a musculoskeletal disease or disorder ameliorated with tizanidine or a pharmaceutically acceptable salt thereof.

11. The method of claim 1, wherein the transdermal patch preparation is applied to the subject once a day.

12. The method of claim 1, wherein the transdermal patch preparation has a surface area of about 10 $cm^2$ to about 200 $cm^2$.

13. The method of claim 1, wherein the transdermal patch preparation further comprises a sorbate component selected from sorbic acid and/or a metal salt of sorbic acid.

14. The method of claim 1, wherein the transdermal patch preparation comprises a support and a drug adhesive matrix on one surface of the support, and wherein the drug adhesive matrix comprises the tizanidine or the pharmaceutically acceptable salt thereof and has a thickness of about 600 μm in a wet state and/or a thickness of about 300 μm in a dry state.

15. The method of claim 1, wherein the transdermal patch preparation comprises a support and a drug adhesive matrix on one surface of the support, and wherein the drug adhesive matrix comprises tizanidine or a pharmaceutically acceptable salt thereof and has a thickness of about 100 to about 400 μm.

\* \* \* \* \*